United States Patent [19]

Strother et al.

[11] 4,364,392

[45] Dec. 21, 1982

[54] DETACHABLE BALLOON CATHETER

[75] Inventors: Charles M. Strother, Madison; Balakrishna V. Kudva, Monona, both of Wis.

[73] Assignee: Wisconsin Alumni Research Foundation, Madison, Wis.

[21] Appl. No.: 212,759

[22] Filed: Dec. 4, 1980

[51] Int. Cl.³ .......................................... A61M 25/00
[52] U.S. Cl. ................................... 128/325; 128/344; 604/98
[58] Field of Search ............ 128/325, 344, 348–350 R, 128/274, 1 R

[56] References Cited

U.S. PATENT DOCUMENTS

| | | | |
|---|---|---|---|
| 3,522,346 | 7/1970 | Chang | 128/214 R X |
| 3,797,485 | 3/1974 | Urquhart | 128/213 |
| 3,834,394 | 9/1974 | Hunter | 128/325 |
| 3,977,409 | 8/1976 | Brendling . | |
| 3,986,213 | 10/1976 | Lynch | 3/36 |
| 4,029,104 | 6/1977 | Kerber . | |
| 4,085,757 | 4/1978 | Pevsner | 128/325 |
| 4,130,114 | 12/1978 | Peeler | 128/274 X |
| 4,143,853 | 3/1979 | Abramson . | |
| 4,202,346 | 5/1980 | Granier | 128/325 |
| 4,205,683 | 6/1980 | O'Neill . | |
| 4,282,875 | 8/1981 | Serbinenro et al. | 128/325 |
| 4,311,146 | 1/1982 | Wonder | 128/325 |
| 4,327,734 | 5/1982 | White | 128/325 |

FOREIGN PATENT DOCUMENTS 542523  5/1973  U.S.S.R. .................... 128/325

OTHER PUBLICATIONS

Luessenhop, "Intra-Arterial Instrumentation for Neurosurgery," Bulletin, Dow Corning, vol. 2, No. 3, Jul. 1960, 128–325.

Primary Examiner—Dalton L. Truluck
Attorney, Agent, or Firm—Isaksen, Lathrop, Esch, Hart & Clark

[57] ABSTRACT

A method and apparatus is disclosed for providing therapeutic occlusions of blood vessels and other body tubular structures using an inflatable balloon (11) mounted at the end of a catheter (15). The balloon (11) and catheter (15) are passed through a blood vessel (12) until the balloon (15) reaches the desired location of the occlusion; a suspension of solid filler particles (27) in a carrier liquid is then pumped through the catheter tube (15) and inflates the blloon (11) until it blocks off the blood vessel. The carrier liquid is forced out through the porous walls of the balloon, leaving a compacted mass of filler particles which will not allow the balloon to shrink. Ridges (20) on the end of the catheter tube (15) engage mating grooves (21) in the neck portion (14) of the balloon structure during insertion and filling of the balloon; the size, shape, and number of these ridges and grooves can be selected to provide a desired force required to detach the catheter tube from the balloon. A valve (18) in the neck portion (14) of the balloon structure allows the particle suspension to pass into the balloon but blocks flow of particles out of the balloon while preferably allowing the carrier liquid to pass therethrough. Medication may be impregnated in either the particles in the balloon or the porous balloon walls to allow controlled release of the medication into the bloodstream.

42 Claims, 10 Drawing Figures

DETACHABLE BALLOON CATHETER

FIELD OF THE INVENTION

This invention pertains generally to the field of catheters used in surgical procedures, and more particularly to inflatable catheters which can be used to occlude a blood vessel or other tubal structure.

BACKGROUND ART

Catheters of various types are commonly used in radiological procedures, and can be produced in small enough sizes to allow insertion into blood vessels. Specially designed catheter systems having a balloon-like structure on their distal ends have found use in occluding blood vessels for therapeutic purposes. The catheter with balloon at its end is inserted into a vein or artery until the balloon reaches the desired point of occlusion, at which time a liquid is pumped through the catheter to inflate the balloon and block the flow of blood. The occlusion of blood vessels in this manner is an alternative to surgery-with its risk, complications and cost-in various medical procedures such as the isolation of bleeding sites, arteriovenous malformations (aneurysms, arteriovenous shunts) and hypervascular tumors.

It is often desirable to provide a permanent occlusion or artificial embolism in the artery supplying the disorder site. Conventional balloon catheter systems are not well adapted to this procedure since the liquid which inflates the balloon can seep out or the surrounding fluid can seep in through the walls of the balloon by osmosis, or the filling liquid can leak out through the valve used to seal off the end of the balloon after the catheter tube is withdrawn. Because conventional inflatable balloon catheters have been unsuited to forming permanent occlusions, a variety of other techniques have been utilized, including the formation of artificial emboli by introducing into the blood vessel an autologous clot or such foreign material as gel foam, lead shot, cotton and wool tails, steel coils and cyanoacrylate.

DESCRIPTION OF THE INVENTION

The balloon catheter apparatus of the invention utilizes an elastic balloon mounted at a neck portion to the end of a catheter tube. The catheter tube and balloon are passed through a vessel until the balloon reaches the desired point, whereupon a suspension of small, solid particles in a carrier liquid is pumped through the tube to inflate the balloon. When the balloon completely closes the blood vessel, the pressure on the fluid suspension is released and a small, leaky valve in the neck portion of the balloon structure closes to prevent the solid particles from discharging while allowing the excess liquid carrier to leak back out. The carrier liquid also leaks out through the walls of the balloon, which are preferably porous. The balloon shrinks slightly until its internal volume is completely occupied by the incompressible particles, thereby providing a permanent blockage of the vessel which will not change in shape over time due to leakage through the balloon walls, as occurs in conventional liquid-filled catheter balloons.

The catheter tube is attached to the neck portion of the balloon such that a predetermined amount of pulling force on the catheter tube will release it from the balloon. In a preferred form, the cylindrical neck has a groove or grooves on its inner surface, and the distal end of the catheter tube has mating ridges formed on its outer surface. The engagement of the ridges with the grooves provides a firm attachment of the catheter tube to the balloon while allowing the tube to be withdrawn when sufficient force is applied to it. The amount of force required to withdraw the tube may be chosen by selecting the rigidity of the material forming the tube ridges and the neck portion as well as by selecting the geometry and size of the grooves and ridges; e.g., rounded ridges and grooves require relatively low withdrawal force, while sharp edged ridges and grooves require a greater force to obtain withdrawal.

The leaky valve which allows one-way passage of filler particles may be formed as a bifurcated cone molded in the bore of the neck portion, extending into the balloon, with a slit cut in the middle of the cone such that the two portions of the cone close to a thin opening narrow enough to prevent the particles from passing through. The bifurcated cone may be forced open by insertion of the distal end of the catheter tube into the cone.

The invention is especially well suited to discharging medication in controlled amounts into the blood stream, since the particles within the balloon may be saturated with medication which leeches into the surrounding liquid, through the walls of the balloon, and into the blood stream, all at a controlled rate. In further specialized embodiments of the invention a portion of the balloon wall is formed of a porous solid material having medication therein which can leech into the bloodstream at a desired rate. The balloon structure may take the shape of a toroid which is inflated to only partially occlude the vessel, allowing blood to flow through the center opening of the toroid. This structure is well adapted to leeching medication into the blood flow, with the medication being held either in the particles which fill the balloon or in medication-impermeated porous walls forming a portion of the balloon walls.

Further objects, features and advantages of the invention will be apparent from the following description taken in conjunction with the drawings showing preferred embodiments of a balloon catheter in accordance with the invention.

BEST MODE FOR CARRYING OUT THE INVENTION

Figure 1:
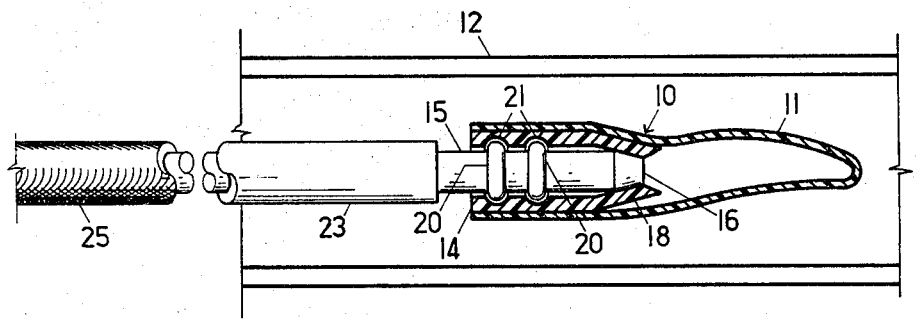
FIG. 1 is a cross-sectional view of a balloon catheter apparatus in accordance with the invention shown illustratively within a blood vessel.

With reference to the drawings, a preferred embodiment of a balloon catheter apparatus in accordance with the invention is shown generally at 10 in FIG. 1. In this view, the balloon portion 11 of the catheter apparatus is shown in deflated form as it is being inserted into a blood vessel 12. The balloon 11 is attached to a generally cylindrical neck portion 14, and a catheter tube 15 is inserted into the bore of the neck 14 such that the beveled distal end 16 of the catheter tube 15 extends into communication with the interior of the balloon 11. The neck portion 14 has a flap-type valve 18 formed on its inner end, with the flaps of the valve being spread apart by the beveled ends 16 of the catheter tube to maintain the valve in a fully opened position.

The catheter tube 15 is releasably secured to the neck portion 14 by means of a pair of ridges 20 formed on the outer periphery of the tube 15 near its distal end and a mating pair of grooves 21 formed around the inner periphery of the neck 14. The engagement of the ridges with the walls of the grooves holds the catheter tube firmly within the neck until sufficient force is exerted on the catheter tube away from the balloon to cause the ridges and the walls of the groove to deform sufficiently to allow the catheter to be pulled out. Generally, the amount of force required to release the catheter tube from the balloon must be less than the drag force that will be experienced by the balloon as it is being placed in position within the blood vessel, but must be low enough so that the catheter can be pulled from the balloon once it is inflated with little or no dragging of the inflated balloon through the blood vessel. It is preferred that the release be obtained by utilizing a second, sleeve catheter 23 which fits around the catheter tube 15 and which will move relative to the tube 15 such that its distal end engages the neck portion 14 to, in effect, push the neck portion away from the end of the catheter tube. The sleeve catheter 23 may be inserted over the catheter tube 15 after the balloon 11 has been placed in its desired position, or the larger sleeve catheter 23 may be inserted into the blood vessel and worked to the desired position with the balloon 11 and catheter tube 15 then being pushed through the sleeve catheter until the balloon 11 exits therefrom. Both the catheter tube 15 and the sleeve catheter 23 are inserted into a blood vessel in a conventional manner using syringes, and the control of fluid to the bore of the inner catheter tube 15 may be accomplished by the use of a conventional Luer lock 25.

The materials of which the various components of the balloon catheter apparatus are formed are preferably selected to be biocompatible—particularly the balloon 11 and the neck portion 14, which ordinarily will be permanently emplaced within the blood vessel. Suitable materials for the balloon 11 and neck portion 14 include segmented polyether polyurethane or silicone rubber, and the catheters 15 and 23 may be formed of similar materials as well as polyethylene, polytetrafluoroethylene, fluorinated ethylene propylene, and other standard biocompatible polymer materials. The balloon 11 and neck portion 14 can be made from two separate parts, as shown in FIG. 1, with the balloon 11 being secured to the outer surface of the neck portion 14 by the use of a biocompatible adhesive. Alternatively, the balloon and neck portion can be formed as a one piece molded unit.

For reasons explained in further detail below, the walls of the balloon 11 are preferably made porous, so that any liquid within the balloon can readily leak out. For example, multiple pores, typically having a pore size of less than 20 microns, can be formed in the balloon (as well as in the walls of the neck portion 14, if desired) by various techniques. Particles such as atomized aluminum powder, glass microspheres, calcium carbonate particles or nylon fibers can be mixed with the liquid polymer material and the mixture poured into a mold. After the material has cured, the particles or fibers embedded in the walls of the balloon can be chemically etched out. A mesh of biocompatible polymer filaments can also be emplaced in the liquid latex of which the balloon is formed so that, after curing, a plurality of windows are left in the balloon material. In another technique, the balloon is first formed and cured, is masked using a mesh having openings of the desired pore size, and is then bombarded with high energy ions in an ion thruster chamber to perforate the balloon wall under the openings in the mask.

The material of the walls of the balloon can also be impregnated with a radiopaque material, such as barium or iodine, to aid in guiding the catheter to the desired position using X-ray fluoroscopy.

Figure 2:
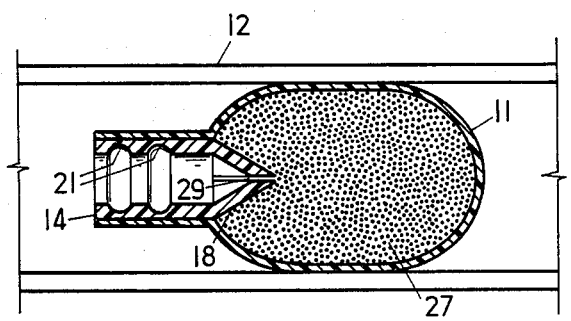
FIG. 2 is a cross-sectional view of the balloon and neck portion of the catheter apparatus of FIG. 1, showing the balloon inflated to occlude the blood vessel.
Figure 3:
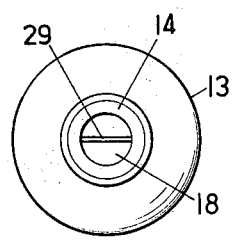
FIG. 3 is a side elevational view of the inflated balloon taken from the left side of the view of FIG. 2.

When the balloon 11 has reached the desired spot within the blood vessel a fluid filling medium composed of a suspension of solid particles in a liquid carrier is pumped through the bore of the inner catheter tube 15 to fill up the balloon 11 such that the walls of the balloon press against the inner walls of the blood vessel, as shown in FIG. 2. The solid filler particles 27 within the balloon may be composed of glass microspheres, carbon microspheres, semi-permeable polymer microspheres, or other solid biocompatible material, having a preferred particle diameter in the range of 50 to 160 microns; the liquid carrier is a bio-compatible liquid such as normal saline-water solution or blood plasma. The viscosity of the carrier liquid and the relative specific gravities of the solid particles and the liquid are selected such that the particles form a homogeneous suspension within the liquid and will flow freely through the relatively small bore of the inner catheter tube 15, which will typically have a diameter in the range of 0.1 mm to 0.4 mm. Although the solid particles 27 are relatively small, they are much larger than the pores in the balloon wall (e.g., the pores are 30 microns in diameter or smaller) so that the liquid carrier in which the particles are suspended can pass through the walls of the balloon while the particles cannot. Continued pumping of the suspension into the balloon eventually pressurizes the balloon to the point where it is completely filled with tightly packed particles. At this point, the balloon is dimensionally stable and will not substantially decrease in size as a result of liquid leakage through the walls of the balloon. In addition, the valve 18 is preferably formed so that a small gap exists in the valve when it is closed so that some of the liquid carrier can leak out of the balloon back into the bore of the catheter tube while the solid particles are blocked. The valve 18 may be simply formed by molding the neck portion 14 on a cylindrical mold having a conical end, resulting in a cone of elastomer material integral with the neck portion 14. The valve is formed by cutting a slit 29 through the middle of the cone; this slit takes out enough material to leave the adjacent facing edges of the bifurcated cone spaced slightly apart—a spacing which is large enough to allow carrier liquid to flow backward but is small enough to block the solid particles within the balloon. The slit 29 formed in the cone is also shown in an end view in FIG. 3.

The balloon 11 is shown in its fully inflated position in FIG. 2 in which it completely occludes the blood vessel 12. In a preferred technique for removing the catheter tube 15 from its engagement with the neck portion 14, an initial pull on the catheter 15 relative to the sleeve catheter 23 causes the ridges 20 to be withdrawn from the grooves 21 and causes the distal end 16 of the catheter to be withdrawn from engagement with the valve 18, although not entirely removed from the bore of the neck portion. Liquid is then withdrawn from the bore of the catheter 15 by the attending physician until blood is observed to exit from the catheter. At this point the neck of the balloon has been fully voided of any stray filler particles and the catheter may be safely withdrawn.

Figure 4:
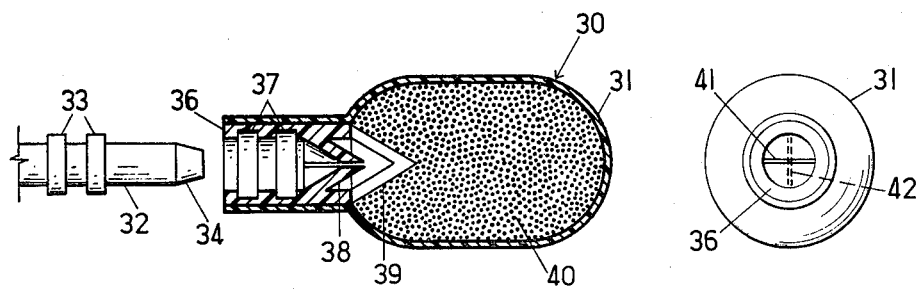
FIG. 4 is a cross-sectional view of the neck and balloon portion of another embodiment of the catheter apparatus of the invention showing the balloon inflated.
Figure 5:
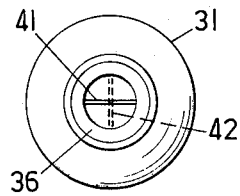
FIG. 5 is a side elevation view of the balloon of FIG. 4 taken from the left side of FIG. 4.

A modification of the balloon catheter apparatus of the invention is shown generally at 30 in FIG. 4, in which the balloon 31 has been fully inflated and the catheter tube 32 has been withdrawn. In this embodiment the catheter tube has a pair of rectangularly shaped, sharp edged ridges 33 formed on its outer periphery near its distal end 34, and the neck portion 36 has a pair of mating rectangular grooves 37 formed in the inner periphery of the generally cylindrical neck bore. The neck portion 36 has a pair of bifurcated cone valves 38 and 39 which have respective slits 41 and 42 therein aligned at right angles to one another to provide a redundant double locking feature which minimizes the likelihood that filler particles will leak out after the catheter tube 32 is withdrawn. The alignment of the slit 41 in the cone valve 38 with the slit 42 in the cone valve 39 is best shown in the end view of FIG. 5.

The structure, materials, and method of use of the balloon catheter apparatus 30 is identical to that for the balloon catheter 10 described above. The rectangular ridges and mating rectangular grooves 37 provide a higher degree of resistance to withdrawal of the catheter tube than do the rounded ridges 20 and grooves 21 for the balloon catheter 10. Although two ridges and two mating grooves are shown for each of the devices described above, it is apparent that a smaller removal force can be achieved by utilizing only one ridge and one mating groove, and that larger removal forces can be achieved by utilizing three or more sets of mating ridges and grooves.

Figure 6:
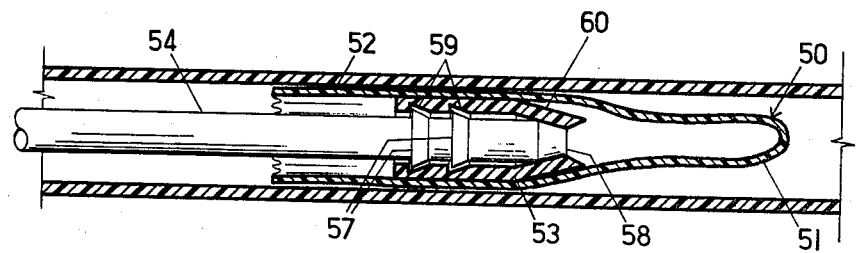
FIG. 6 is a cross-sectional view of another embodiment of balloon catheter apparatus in accordance with the invention.
Figure 7:
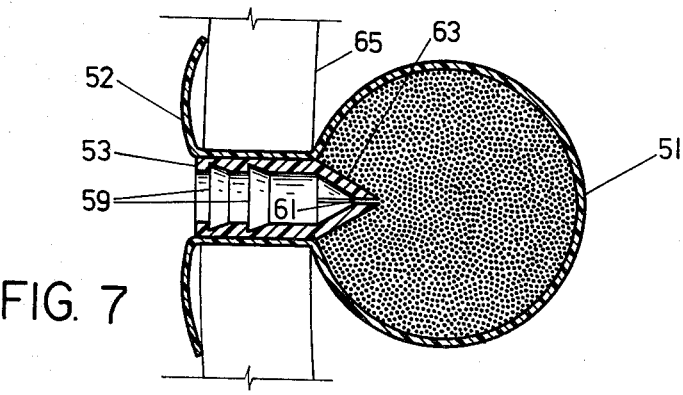
FIG. 7 is a cross-sectional view of the neck and balloon portion of the catheter apparatus of FIG. 6, showing the balloon inflated and illustratively positioned to close a tear in a blood vessel wall.

Another modified embodiment is shown generally at 50 in FIG. 6. In this version, the balloon 51 includes a circular disc or skirt 52 which extends from the periphery of the cylindrical neck 53 to which the balloon 51 is attached. The view of FIG. 6 shows the skirt 52 collapsed behind the balloon 51 as the apparatus is being pushed through a vessel. Two triangularly shaped ridges 57 extend from the outer periphery of the catheter tube 54 near its distal end 58 and mate with corresponding triangularly shaped grooves 59 in the inner surface of the neck 53. As best shown in FIG. 7, a bifurcated cone valve 60 having a center slit 61 holds the filler particles within the balloon while allowing the liquid carrier to leak out.

A cross-sectional view of the inflated balloon 51 with its depending skirt 52 spread out is shown in FIG. 7. The material of the skirt 52, which may be formed integrally with the balloon 51, is very flexible so that it can be collapsed inwardly during insertion, as shown in FIG. 6, and then spread out at the desired location to a diameter which is greater than the normal diameter of a non-fully inflated balloon. For example, the balloon may be worked to the site of a tear in a blood vessel 65 and may be partially carried through the tear opening by the flow of blood leaking out of the vessel. The balloon may then be inflated outside of the vessel 61 to immobilize the balloon, and the skirt 52 may then spread open within the vessel to block the tear opening, as illustrated in FIG. 7.

The triangularly shaped ridges 57, with their mating grooves 59, provide a withdrawal force required to release the catheter tube from the neck portion which is intermediate that provided from rounded ridges and grooves and that provided from rectangular ridges and grooves. The triangular ridges 57 will more readily bend and deform in order to allow the catheter to be removed than will the square ridges 33 on the catheter tube 32.

Figure 8:
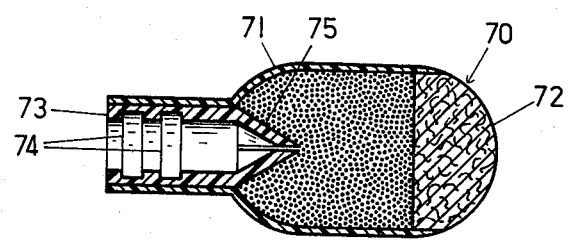
FIG. 8 is a cross-sectional view of another embodiment of the balloon and neck portion of the catheter apparatus of the invention in which a plug of porous material forms part of the wall of the balloon.

Another modified embodiment of a balloon structure for use in the catheter apparatus of the invention is shown generally at 70 in FIG. 8, and includes a flexible balloon wall portion 71 of generally cylindrical shape and a plug 72 of porous polymer material which closes off the distal end of the cylindrical balloon portion 71. The balloon structure also includes a neck portion 73 which has a pair of rectangularly shaped grooves 74 formed in its inner surface and a bifurcated cone valve 75 blocking the bore of the neck 73. Although not shown in FIG. 8, a catheter tube—in construction and use identical to the catheter tube 32 of FIG. 4—is adapted to be inserted into the bore of the neck portion 73 and have its ridges engage with the walls of the grooves 74. The balloon formed of the cylindrical portion 71 and the plug 72 is inflated by injection of a filler particle suspension as described above, and the preferred materials of the balloon and the neck portion 73 are identical to those materials described above for the balloon catheter apparatus 10.

The polymer plug 72 allows liquid to readily pass in and out of the balloon. Thus, the carrier liquid within the balloon can discharge through the plug 72 into the blood stream, and blood fluids can also pass through the plug into the balloon so that medication held within the particles can leech out into the bloodstream. The plug 72 itself can be impregnated with a medication which will migrate into the blood stream at a controlled rate.

Figure 9:
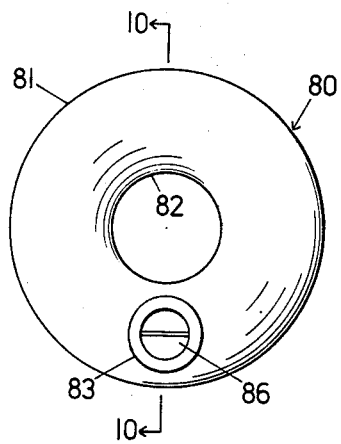
FIG. 9 is a front elevation view of the neck and balloon portion of another embodiment of the catheter apparatus of the invention which has the shape of a toroid.
Figure 10:
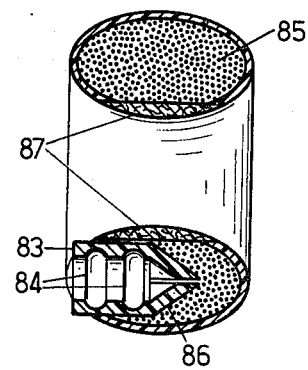
FIG. 10 is a cross-sectional view of the balloon of FIG. 9 taken along the lines 10—10 of FIG. 9.

A further modification of a balloon structure for a catheter in accordance with the invention is shown generally at 80 in FIG. 9. The balloon portion 81, when inflated, has the shape of a toroid with a central opening 82 through which blood may flow. Thus, the structure 80 does not entirely occlude a blood vessel but rather restricts the flow of blood therethrough. A catheter tube (not shown) is used to place the uninflated balloon at the desired spot in the artery and is releasably secured, in the manner described above, to a neck portion 83 which is mounted to the balloon 81 parallel to the axis of the hole 82 in the balloon. The neck portion 83 has a pair of grooves 84 which mate with corresponding ridges on the catheter tube, and the backflow of filler particles 85 within the inflated balloon is blocked by a bifurcated cone valve 86. The walls of the balloon 81 facing the opening 82 are formed of a porous polymer material 87 such that liquid can readily flow into and out of the interior of the balloon; whereby medication impregnated in the filler particles 85, or in the porous plug material 87 itself, can migrate into the blood stream as blood flows through the opening 82. Even without the use of the porous plug 87, the toroidal catheter structure 80 can effectively discharge controlled amounts of medication into the bloodstream where the walls of the balloon are themselves porous enough to allow seepage of the medication through the walls into the bloodstream. As described above, the pore size in the walls is maintained small enough so that the filler particles do not escape.

It is understood that the invention is not confined to the particular construction and arrangement of parts herein illustrated and described, but embraces such modified forms thereof as come within the scope of the following claims.

We claim:

1. Balloon catheter apparatus comprising:
   (a) an inflatable balloon of biocompatible elastic material;
   (b) a neck portion attached to the balloon and having an interior bore opening into the interior of the balloon;
   (c) small, flowable solid filler particles in a carrier liquid filling the interior of the balloon, the filler particles packed to maintain the balloon in substantially inflated shape;
   (d) valve means in the neck portion for opening to allow passage of a suspension of the solid filler particles in a carrier liquid into the interior of the balloon and closing to prevent the discharge of the particles out of the interior of the balloon;
   (e) a catheter tube adapted to fit into the bore of the neck portion and having an interior bore through which a suspension of the solid particles in a carrier liquid can be pumped through the valve means and into the interior of the balloon; and
   (f) means for releasably securing the catheter tube to the neck portion so that the catheter tube will be released when a pulling force is applied to the catheter tube which is greater than a selected minimum force.

2. The catheter apparatus of claim 1 wherein the filler particles are microspheres having a diameter between 50 and 160 microns.

3. The catheter apparatus of claim 1 wherein in the filler particles are microspheres formed of a material selected from the group consisting of glass, radiopaque glass, carbon, and semipermeable, biocompatible polymers.

4. The catheter apparatus of claim 1 wherein the balloon and neck portion are formed of a material selected from the group consisting of silicone rubber and segmented polyether polyurethane.

5. The catheter apparatus of claim 1 wherein the valve means allows carrier liquid to leak from the balloon through the valve means while blocking passage of the filler particles.

6. The catheter apparatus of claim 1 wherein the carrier liquid is selected from the group consisting of saline solution and blood plasma.

7. The catheter apparatus of claim 1 wherein the elastic material of the balloon has pores therein to allow the carrier liquid inside to leak out, the size of the pores being smaller than the size of the filler particles so that the particles do not leak out.

8. The catheter apparatus of claim 7 wherein the pores in the balloon are not greater than 20 microns in diameter.

9. The catheter apparatus of claim 1 including a second bifurcated cone of elastomer material attached to the neck portion and blocking its bore with the apex of the cone extending toward the interior of the balloon, the second cone valve having a center slit which divides the cone into two portions spaced apart a distance less than the diameter of the filler particles when the valve is closed to thereby allow liquid to pass out but blocking the passage of filler particles.

10. The catheter apparatus of claim 1 wherein the catheter tube has a beveled edge leading to its distal end which is adapted to engage the two portions of the cone valve and spread them apart to fully open the valve and allow the suspension of filler particles to flow freely from the catheter tube into the interior of the balloon.

11. The catheter apparatus of claim 1 wherein the balloon is generally cylindrical in shape, has a closed end and an open end, and wherein the neck portion has a cylindrical exterior surface and the balloon portion is attached to this exterior surface.

12. The catheter apparatus of claim 1 wherein a plug of porous polymer material forms a portion of the wall of the balloon and allows liquid to pass through the porous polymer plug while blocking the passage of filler particles.

13. The catheter apparatus of claim 1 wherein the balloon has a toroidal shape when inflated with a suspension of filler particles in carrier liquid and wherein a portion of the walls of the balloon are formed of a plug of porous polymer material which allows carrier liquid to pass therethrough while blocking the passage of filler particles.

14. The catheter apparatus of claim 12 or 13 wherein the porous plug is impregnated with a medication which will migrate into the liquid surrounding the balloon at a controlled rate.

15. The catheter apparatus of claim 1 wherein the filler particles are impregnated with medication and wherein the walls of the balloon are porous to allow the carrier liquid to pass therethrough while blocking the passage of the filler particles, whereby the medication in the filler particles can disperse through the walls of the balloon into surrounding liquid at a controlled rate.

16. The catheter apparatus of claim 1 wherein the neck portion has a cylindrical inner surface and wherein the means for releasably securing the catheter tube to the neck portion comprises at least one ridge formed on the periphery of the catheter tube and at least one groove formed in the inner surface of the neck portion which mates with the ridge on the catheter tube to cause the catheter tube to be releasably locked to the neck portion.

17. The catheter apparatus of claim 16 wherein the ridge on the catheter tube and the mating groove in the neck portion are semi-circular in cross-section.

18. The catheter apparatus of claim 16 wherein the ridge on the catheter tube and the mating groove in the neck portion are rectangular in cross-section.

19. The catheter apparatus of claim 16 wherein the ridge on the catheter tube and the mating groove in the neck portion are triangular in cross-section.

20. The catheter apparatus of claim 16 wherein the number and shape of the ridges on the catheter tube and the mating grooves in the neck portion yield a selected minimum force required to detach the catheter tube from the neck portion.

21. The catheter apparatus of claim 1 including a sleeve catheter fitting over the catheter tube, whereby the neck portion can be engaged by the sleeve catheter to hold it while the catheter tube is pulled out of the bore of the neck portion.

22. An inflatable catheter balloon structure attachable to the end of a catheter tube for inflation with solid filler particles to occlude a body vessel, comprising:
   (a) an inflatable balloon of biocompatible elastic material;
   (b) a neck portion attached to the balloon and having an interior bore opening into the interior of the balloon;
   (c) valve means, attached to the neck portion and blocking the bore thereof, for opening to allow passage of fluid into the interior of the balloon and closing to restrict the discharge of filler particles from within the balloon which are larger than a preselected size but allowing liquid to leak back through the valve out of the balloon; and
   (d) means for releasably securing a catheter tube to the neck portion.

23. The catheter balloon structure of claim 22 wherein the elastic material of the balloon has pores therein to allow the carrier liquid inside to leak out, the size of the pores being smaller than the size of the filler particles so that the particles do not leak out.

24. The catheter balloon structure of claim 22 including filler particles in a carrier liquid filling the interior of the balloon wherein the filler particles are microspheres having a diameter between 50 and 160 microns.

25. The catheter balloon structure of claim 24 wherein the filler particles are formed of a material selected from the group consisting of glass, radiopaque glass, carbon, and semipermeable, biocompatible polymers.

26. The catheter balloon structure of claim 22 wherein the balloon and neck portion are formed of a material selected from the group consisting of silicone rubber and segmented polyether polyurethane.

27. The catheter balloon structure of claim 23 wherein the pores in the balloon are not greater than 20 microns in diameter.

28. The catheter balloon structure of claim 22 including a second bifurcated cone of elastomer material attached to the neck portion blocking its bore with the apex of the cone extending toward the interior of the balloon, the second cone valve having a center slit which divides the cone into two portions spaced apart a distance less than the diameter of the filler particles when the valve is closed to thereby allow liquid to pass out but blocking the passage of filler particles.

29. The catheter balloon structure of claim 22 wherein the balloon is generally cylindrical in shape, has a closed end and an open end, and wherein the neck portion has a cylindrical exterior surface and the balloon is attached to this exterior surface.

30. The catheter balloon structure of claim 22 wherein a plug of porous polymer materials forms a portion of the wall of the balloon and allows liquid to pass through the porous polymer plug while blocking the passage of filler particles.

31. The catheter balloon structure of claim 22 wherein the balloon has a toroidal shape when inflated with a suspension of filler particles in carrier liquid and wherein a portion of the walls of the balloon are formed of a plug of porous polymer material which allows carrier liquid to pass therethrough while blocking the passage of filler particles.

32. The catheter balloon structure of claim 30 or 31 wherein the porous plug is impregnated with a medication which will migrate into the liquid surrounding the balloon at a controlled rate.

33. The catheter balloon structure of claim 24 wherein the filler particles are impregnated with medication, whereby the medication in the filler particles can disperse through the walls of the balloon into surrounding liquid at a controlled rate.

34. The catheter balloon structure of claim 22 wherein the neck portion has a cylindrical inner surface and wherein the means for releasably securing a catheter tube to the neck portion comprises at least one groove formed in the inner surface of the neck portion which is adapted to mate with a ridge formed on the catheter tube to cause the catheter tube to be releasably locked to the neck portion.

35. The catheter balloon structure of claim 34 wherein the groove in the neck portion is semi-circular in cross-section.

36. The catheter balloon structure of claim 34 wherein the groove in the neck portion is rectangular in cross-section.

37. The catheter balloon structure of claim 34 wherein the groove in the neck portion is triangular in cross-section.

38. A method of occluding a blood vessel, comprising the steps of:
   (a) inserting a catheter tube with an inflatable balloon at its distal end into a blood vessel until the desired point of occlusion is reached by the balloon;
   (b) injecting a suspension of solid filler particles in a carrier liquid through the bore of the catheter tube and into the balloon to fill up the balloon until the balloon blocks off flow through the blood vessel;
   (c) withdrawing the catheter tube from the balloon to leave the balloon blocking the blood vessel; and
   (d) leaking the carrier liquid from the interior of the balloon while preventing the passage of the solid filler particles out of the interior of the balloon.

39. Balloon catheter apparatus comprising:
   (a) an inflatable balloon of biocompatible elastic material;
   (b) a neck portion attached to the balloon and having an interior bore opening into the interior of the balloon;
   (c) small, flowable solid filler particles filling the interior of the balloon to maintain the balloon in substantially inflated shape;
   (d) valve means in the neck portion for opening to allow passage of a suspension of the solid filler particles in a carrier liquid into the interior of the balloon and closing to prevent the discharge of the particles out of the interior of the balloon, the valve means comprising a bifurcated cone of elastomer material attached to the neck portion and blocking the bore thereof with the apex of the cone extending toward the interior of the balloon, the cone having a center slit which divides the cone into two portions which are spaced apart a distance less than the diameter of the filler particles when the valve is closed to thereby allow liquid to pass out of the balloon but blocking the passage of the filler particles;

(e) a catheter tube adapted to fit into the bore of the neck portion and having an interior bore through which a suspension of the solid particles in a carrier liquid can be pumped through the valve means and into the interior of the balloon; and (f) means for releasably securing the catheter tube to the neck portion so that the catheter tube will be released when a pulling force is applied to the catheter tube which is greater than a selected minimum force.

40. Balloon catheter apparatus comprising:
(a) an inflatable balloon of biocompatible elastic material;
(b) a neck portion attached to the balloon and having an interior bore opening into the interior of the balloon;
(c) small, flowable solid filler particles filling the interior of the balloon to maintain the balloon in substantially inflated shape;
(d) valve means in the neck portion for opening to allow passage of a suspension of the solid filler particles in a carrier liquid into the interior of the balloon and closing to prevent the discharge of the particles out of the interior of the balloon;
(e) a catheter tube adapted to fit into the bore of the neck portion and having an interior bore through which a suspension of the solid particles in a carrier liquid can be pumped through the valve means and into the interior of the balloon;
(f) means for releasably securing the catheter tube to the neck portion so that the catheter tube will be released when a pulling force is applied to the catheter tube which is greater than a selected minimum force; and
(g) a disc of flexible material extending out from the periphery of the neck portion and having a diameter when extending radially outward from the neck portion which is greater than that of the unfilled balloon.

41. An inflatable catheter balloon structure attachable to the end of a catheter tube for inflation with solid filler particles to occlude a body vessel, comprising:

(a) an inflatable balloon of biocompatible elastic material;
(b) a neck portion attached to the balloon and having an interior bore opening into the interior of the balloon;
(c) valve means, attached to the neck portion and blocking the bore thereof, for opening to allow passage of fluid into the interior of the balloon and closing to restrict the discharge of filler particles from within the balloon which are larger than a preselected size but allowing liquid to leak back through the valve out of the balloon, the valve means comprising a bifurcated cone of elastomer material attached to the neck portion blocking the bore thereof with the apex of the cone extending toward the interior of the balloon, the cone having a center slit which divides the cone into two portions which are spaced apart a distance less than the diameter of the filler particles when the valve is closed to thereby allow liquid to pass out of the balloon but blocking passage of the filler particles;
(d) means for releasably securing a catheter tube to the neck portion.

42. An inflatable catheter balloon structure attachable to the end of a catheter tube for inflation with solid filler particles to occlude a body vessel, comprising:
(a) an inflatable balloon of biocompatible elastic material;
(b) a neck portion attached to the balloon and having an interior bore opening into the interior of the balloon;
(c) valve means, attached to the neck portion and blocking the bore thereof, for opening to allow passage of fluid into the interior of the balloon and closing to restrict the discharge of filler particles from within the balloon which are larger than a preselected size but allowing liquid to leak back through the valve out of the balloon;
(d) means for releasably securing a catheter tube to the neck portion; and
(e) a disc of flexible material extending out from the periphery of the neck portion and having a diameter when extending radially outward from the neck portion which is greater than that of the unfilled balloon.

* * * * *

UNITED STATES PATENT AND TRADEMARK OFFICE
CERTIFICATE OF CORRECTION

PATENT NO. : 4,364,392
DATED : December 21, 1982
INVENTOR(S) : Charles M. Strother, et al It is certified that error appears in the above-identified patent and that said Letters Patent are hereby corrected as shown below:

ON THE TITLE PAGE,
In the abstract, line 9, change "blloon" to --balloon--.

Claim 9, line 1, after "claim" change "1" to --39--.

Claim 10, line 1, after "claim" change "1" to --39--.

Claim 28, line 1, after "claim" change "22" to --41--.

Signed and Sealed this

Twenty-ninth Day of March 1983

[SEAL]

Attest:

GERALD J. MOSSINGHOFF

Attesting Officer     Commissioner of Patents and Trademarks